(12) United States Patent
Roberts et al.

(10) Patent No.: US 7,244,707 B2
(45) Date of Patent: Jul. 17, 2007

(54) REGULATION OF CYTOTROPHOBLAST CELL DIFFERENTIATION AND CELL MIGRATION

(75) Inventors: Claire Roberts, Adelaide (AU); Phillip Owens, Cheongju (KR)

(73) Assignee: Adelaide Research & Innovation Pty Ltd, South Australia (AU)

( * ) Notice: Subject to any disclaimer, the term of this patent is extended or adjusted under 35 U.S.C. 154(b) by 0 days.

(21) Appl. No.: 10/789,105

(22) Filed: Feb. 27, 2004

(65) Prior Publication Data

US 2005/0100549 A1 May 12, 2005

Related U.S. Application Data

(63) Continuation of application No. PCT/AU02/01226, filed on Aug. 30, 2002.

(30) Foreign Application Priority Data

Aug. 30, 2002 (AU) ..................... PR7331

(51) Int. Cl.
*A61K 38/18* (2006.01)
(52) U.S. Cl. .................... 514/12; 424/145.1
(58) Field of Classification Search ............ None
See application file for complete search history.

(56) References Cited

U.S. PATENT DOCUMENTS 5,420,111 A * 5/1995 Gluckman et al. ............ 514/12

OTHER PUBLICATIONS

Behr and Wang. Eur J Obstet Gynecol Reprod Biol. Jul. 1, 2004;115 Suppl 1:S72-6.*
C. o'Neill Biol. Reprod. 1997 56:229-237.*
Olson et al. The EMBO Journal. 2004; 23: 2019-2028.*
Villevalois-Cam et al. Journal of hepatology. 2003: 38: 156-163.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Tseng et al. Frontiers in Bioscience. 2002; 7: d1566-d1574.*
Gratton et al. Placenta. 2002: 23: 303-310—see abstract.*
Kim et al., Fertil. Steril. 1000; 73: 5: 996-1000.*
Sohlström et al. Growth Hormone & IGF Research 2001, 11; 392-398.*

* cited by examiner

Primary Examiner—Elizabeth Kemmerer
Assistant Examiner—Christina Borgeest
(74) Attorney, Agent, or Firm—Francis LawGroup

(57) ABSTRACT

The present invention is predicated on the discovery of certain interactions between cellular growth factors and opposing actions that control differentiation and migration or invasion of cytotrophoblasts into the uterine endometrium during pregnancy. IGF-II and latent transforming growth factor beta (TGFβ), the inactive precursor of TGFβ, compete for binding to the CIM6P receptor. IGF-II prevents latent TGFβ binding to the CIM6P receptor. The invention therefore offers a method of regulating and directing cytotrophoblast differentiation and function based on the interaction between IGF-II, latent TGFβ and the CIM6P receptor. There is disclosed a method of regulating cytotrophoblast and stem cell differentiation and migration characterized by adjusting levels of insulin-like growth factor II (IGF-II) available for binding to the cation-independent mannose-6-phosphate (CIM6P) receptor. The discovery may be applied to embryonic or adult stem cells to control their differentiation and migratory behaviour.

6 Claims, 13 Drawing Sheets

Denotes significantly different from control (p<0.05).

*Denotes significantly different from control (p<0.05).

*Denotes significantly different from control p<0.05

**Denotes significantly different from control (p=0.001).

*Denotes significantly different from control (p=0.026).

Figure 12 Note this figure has been replaced due to error in legend

*Denotes significantly different from control (p=0.026).

SEQUENCE LISTING

<160> NUMBER OF SEQ ID NOS: 2

<210> SEQ ID NO 1
<211> LENGTH: 16
<212> TYPE: DNA
<213> ORGANISM: Artificial
<220> FEATURE:
<223> OTHER INFORMATION: IGF-II forward primer

<400> SEQUENCE: 1
cccctccgac cgtgct                                                    16

<210> SEQ ID NO 2
<211> LENGTH: 25
<212> TYPE: DNA
<213> ORGANISM: Artificial
<220> FEATURE:
<223> OTHER INFORMATION: IGF-II reverse primer

<400> SEQUENCE: 2
tggatggact gcttccaggt gtcat                                          25

REGULATION OF CYTOTROPHOBLAST CELL DIFFERENTIATION AND CELL MIGRATION

This application a continuation application of International Application No. PCT/AU02/01226, filed Aug. 30, 2002.

FIELD OF THE INVENTION

The present invention relates to the use of a method to adjust the behaviour of cytotrophoblast cells of the placenta and that of stem cells. In particular the invention is concerned with the regulation of their differentiation and migration.

BACKGROUND OF THE INVENTION

During embryo implantation and placentation, cytotrophoblast cells of the conceptus proliferate and migrate. Growth factors induce cytotrophoblasts to replicate, and to increase the number of cytotrophoblasts that migrate into the uterine endometrium. During this process cytotrophoblasts sequentially attach (adhere) and detach (de-adhere) from surrounding cells and extracellular matrix. Migrating cytotrophoblasts also secrete extracellular matrix to which they can adhere, as well as proteolytic enzymes that degrade the extracellular matrix from which they detach and through which they migrate. Similar processes occur during differentiation of stem cells in the embryo, fetus, child, and adult.

In many biological processes, cells change or differentiate from one cell type to another in response to growth factor polypeptides and glycoproteins. In mammals, these growth factors may either originate from the progenitor cell undergoing differentiation (autocrine mechanism) or from neighbouring cells (paracrine mechanism). These biological processes include those that occur during normal mammalian development in which cells of different types in the conceptus change into other cell types that form the placenta, tissues and organs of the embryo, the fetus, and eventually the adult.

The differentiation pathway of cytotrophoblasts and embryonic and adult stem cells includes migration from one site to another. This can include invasion by the migrating cells into a tissue or organ comprised of or constructed by cells of other types or lineages.

Cells of all types proliferate and migrate during organogenesis and to increase the size of the tissue during normal development and growth in embryonic/fetal life and throughout childhood.

Embryonic stem cells are pluripotent cells derived from the inner cell mass of the early mammalian embryo from which all cell types of the embryo and all endodermal and mesodermal cells in the extra-embryonic tissues are derived. In vivo they differentiate in a low oxygen environment during the first third of pregnancy in humans and other mammals.

Adult stem cells are pluripotent cells found in all mammalian tissues from which many or all cell lineage types of the body may differentiate.

Cytotrophoblast cells are derived from extra-embryonic ectodermal cells of the conceptus, which comprise the trophectoderm of the blastocyst. Cytotrophoblast cells are therefore an epithelial cell type. Cytotrophoblast cells migrate into the endometrium of the maternal uterine decidua to form the placenta. Within the exchange region of the placenta cytotrophoblast cells, known as villous cytotrophoblasts, retain their epithelial phenotype. However, invasive cytotrophoblasts, also known as extravillous cytotrophoblasts, have undergone epithelial-mesenchymal transition, a process which allows them to assume a migratory phenotype. Invasion of the maternal decidua by cytotrophoblast cells is terminated by fusion of cytotrophoblast cells to form multinucleate cells called placental bed giant cells.

Under specific conditions cytotrophoblasts and stem cells, both embryonic and adult, are able to synthesise and secrete insulin-like growth factor II (IGF-II). These processes occur in a low oxygen environment.

Since the IGF-II gene is imprinted and expressed by the paternal allele, the paternal genotype is important in determining the capacity of the placenta, the genotype of which is a combination of the paternal and maternal genotypes, to synthesise IGF-II. It is known that there are polymorphisms in the IGF-II gene which may determine the capacity of tissues to synthesise IGF-II. Since the placenta synthesises abundant IGF-II it was postulated that mutations in the IGF-II gene may lead to pre-eclampsia. A common Apa I restriction fragment length polymorphism in exon 9 of the IGF-II gene was investigated as a possible mutation which causes pre-eclampsia (Bermingham et al. 2000). It was unequivocally shown that this polymorphism in the IGF-II gene is not involved in pre-eclampsia. The authors concluded that IGF-II does not play a role in the aetiology of pre-eclampsia. As there are other polymorphisms in this gene and neighbouring genes which determine the capacity of the placenta to synthesise IGF-II, and hence its capacity to invade the uterine decidua and establish optimal placental function, we claim that IGF-II plays a determining role in pre-eclampsia.

Expression of IGF-II is affected by a functional polymorphism of the insulin (INS) variable number of tandem repeats (VNTR) locus in humans. In Caucasians, the INS VNTR micro satellite divides into two classes of alleles which vary in size. Class I alleles (26-63 repeat units) have been strongly associated with insulin dependent diabetes mellitus (Bennett & Todd 1996), while Class III alleles protect against IDDM but are associated with non-insulin dependent diabetes mellitus (Ong et al. 1999). The INS VNTR has been shown to be a long range control element for both insulin and IGF-II.

All nucleated cells in the body have the capacity to detect oxygen concentration and respond accordingly. Chronic reductions in oxygen concentration within the cell result in new gene expression which is mediated by several transcription factors. Hypoxia inducible factor-1 (HIF-1) is an oxygen-sensitive transcription factor which regulates gene expression in response to low cellular oxygen concentration. HIF-1 activates the transcription of a variety of target genes whose protein products are involved in angiogenesis, cell proliferation and viability, and vascular remodelling. HIF-1, also known as ARNT, is constitutively expressed and must bind to HIF-1, which is regulated by hypoxia (Huang et al. 1996), before binding to DNA as a heteromeric complex (Wang et al. 1995). IGF-II is a target gene for HIF-1 and is thought to be both regulated by, and a regulator of, HIF-1 (Feldser et al. 1999). Feldser et al. reported that in normoxic conditions insulin, IGF-I and IGF-II all induce HIF-1 protein expression resulting in transcription of its target genes including IGF-II, IGFBP-2 and IGFBP-3. When human chorionic villous explants were cultured in 2% $O_2$ and compared with those cultured in 20% $O_2$ cytotrophoblast proliferation was increased nearly 3-fold (Genbacev et al. 1997). In cultured human villous explants HIF-1 transcription was stimulated by low oxygen tension (3% $O_2$) and cytotrophoblast proliferation ensued (Caniggia et al. 2000).

SUMMARY OF THE INVENTION

The present invention is predicated on the discovery of certain interactions between cellular growth factors and opposing actions that control differentiation and migration or invasion of cytotrophoblasts into the uterine endometrium which, during pregnancy, is called the decidua. In addition, this discovery may be applied to embryonic or adult stem cells to control their differentiation and migratory behaviour.

Therefore, according to a first aspect of the present invention, although this need not be the broadest nor indeed the only aspect of the invention there is provided a method of regulating cytotrophoblast and stem cell differentiation and migration consisting of adjusting levels of IGF-II available for binding to the cation-independent mannose-6-phosphate (CIM6P) receptor.

We have discovered that IGF-II and latent transforming growth factor beta (TGF), the inactive precursor of TGF, compete for binding to the CIM6P receptor. IGF-II prevents latent TGF binding to the CIM6P receptor. It is known that binding of latent TGF to the CIM6P receptor leads to the production of active TGF by the urokinase plasminogen activator (uPA) system (Godar et al. 1999). It is suggested that IGF-II prevents activation of latent TGF. Cells that produce sufficient amounts of IGF-II, or cells that are exposed to sufficient amounts of IGF-II, therefore cannot convert latent TGF into its active form (TGF) by the uPA system that forms a complex with the CIM6P receptor on the surface of the cell.

The present invention therefore offers a method of regulating and directing cytotrophoblast differentiation and function based on the interaction between IGF-II, latent TGF and the CIM6P receptor.

During pregnancy in humans, IGF-II is produced by cytotrophoblast cells and is most abundantly expressed at the invasive front. It is known that TGF promotes terminal differentiation in these cells, thus inhibiting their migratory behaviour.

We have discovered that IGF-II binding to the CIM6P receptor prevents local activation of TGF. In cytotrophoblast cells, IGF-II thereby prevents migratory or invasive mesenchymal-type cytotrophoblast cells from differentiating into non-migratory or non-invasive giant cell types.

Competition for binding the CIM6P receptor is dependent on the concentration of IGF-II and the concentration of latent TGF in the vicinity of cytotrophoblasts. The CIM6P receptors on the surface of cytotrophoblasts that produce sufficient quantities of IGF-II or are exposed to sufficient amounts of IGF-II are unable to bind latent TGF. In this way IGF-II prevents cytotrophoblasts from activating latent TGF. In the presence of sufficient IGF-II these cells therefore maintain their mesenchymal type and migratory activity.

Removal of IGF-II permits these cells to activate latent TGF. The action of TGF converts these cells into non-replicating and non-migratory types.

It will be appreciated that in the placenta the promotion of cytotrophoblast migration is highly desirable. It will also be appreciated that the application of stem cell technology to treat disease may require promotion of epithelial-mesenchymal transition or its inhibition depending on the direction of stem cell differentiation required.

Thus, in a first preferred form of the invention there is provided a method of promoting invasive and migratory cell behaviour by exposing cytotrophoblasts or stem cells (embryonic or adult) to elevated levels of IGF-II, such that the cell CIM6P receptors are unable to bind latent TGFβ.

In reproduction treatment with insulin-like growth factor II (IGF-II) promotes implantation and placentation:

Insulin-like growth factor II treatment of embryos promotes conversion of trophectoderm cells into cytotrophoblast cells thereby increasing the success of implantation of embryos into the uterine decidual endometrium, thereby increasing the success of formation of a viable placenta, and thereby improving the rate of successful pregnancy.

Addition of insulin-like growth factor II to embryos produced by in vitro fertilisation techniques can be used to treat infertility. Thus, treatment of pregnant women or their embryos with insulin-like growth factor II can be used to prevent recurrent spontaneous miscarriage and to prevent pre-eclampsia.

Further, administration of IGF-II to pregnant women or their embryos may prevent intrauterine growth restriction or be used to treat placental abruption.

Treatment of embryonic stem cells or adult stem cells with insulin-like growth factor II or culture in a hypoxic environment (1% oxygen) which increases their synthesis of insulin-like growth factor II, promotes their differentiation into mesodermal/mesenchymal cell types.

In a further form of the invention there is provided a method of inhibiting stem cell division, stem cell migration and promoting terminal differentiation behaviour by exposing said stem cell to reduced levels of IGF-II, such that the stem cell CIM6P receptors are able to bind latent TGFβ and thereby promote the activation of TGFβ.

Thus, treatment of embryonic stem cells or adult stem cells with inhibitors of IGF-II action on CIM6P receptor (for example soluble CIM6P receptor or fragments thereof) will promote their differentiation into epithelial cell types, including neurones or their precursors.

The invention is, in a further aspect exemplified by the use of not only IGF-II in its basic form, but also to naturally occurring precursors of and isomers of IGF-II. Similarly, the treatments identified above may be carried out also using synthetic analogues of IGF-II that have altered ability to bind to type-1 IGF receptors, altered ability to bind to insulin receptors, altered ability to bind to IGF-binding proteins and increased ability to bind to cation-independent mannose-6-phosphate receptors (also known as CIM6P receptors, type-2 IGF receptors and IGF-II receptors).

Still further aspects of the invention are concerned with diagnostic uses of IGF-II and the recognition that variation in the capacity of the placenta to produce IGF-II allows predictions to be made concerning the differentiation/migration behaviours to be expected from cytotrophoblasts and therefore the capacity of the placenta to sustain a healthy pregnancy.

Thus, in accordance with a still further aspect of the invention measurement of the composition of and the sequence of nucleotides in the deoxyribonucleic acid near the insulin-like growth factor II gene in human embryos can be used to diagnose their ability to establish successful healthy pregnancy. In particular, the sequence of nucleotides known as the insulin (INS) variable number of tandem repeats (VNTR), which is known to determine placental production of IGF-II, specifically determines the capacity of cytotrophoblasts to synthesize IGF-II and hence determines their capacity to migrate into the uterine decidua and therefore determines the capacity of the placenta to transport substrates to the embryo/fetus.

Alternatively, determination of the nucleotide sequence of the same gene locus INS VNTR on biological specimens (for example blood) from both the mother and the father can be used to diagnose their ability to establish successful healthy pregnancy.

Similarly, measurement of the amount of messenger ribonucleic acid transcribed from the insulin-like growth factor II gene in human embryos can be used to diagnose their ability to establish successful healthy pregnancy.

Measurement of the amount of insulin-like growth factor II protein secreted by human embryos can also be used to diagnose their ability to establish successful healthy pregnancy.

The measurements as described above may be performed on a specimen obtained from either or both biological parents of a human embryo and can be used to diagnose their ability to establish successful healthy pregnancy. This information can thus be used to assist in identifying those individuals who are likely to derive most benefit from treatment according to the methods of the invention.

It should be noted that the methods of the invention may be used in humans as well as in other mammalian species, such as the horse, cow, sheep, goat and pig.

The action of IGF-II in regulating cytotrophoblast differentiation/migration is provided below. IGF-II is produced by cytotrophoblast cells. These cells are known to have receptors able to bind IGF-II (Rebourcet et al. 1998). These receptors include type-1 IGF receptors, which bind IGF-1, IGF-II and insulin. In many cell types, binding of IGF-1, IGF-II or insulin to the type-1 IGF receptor promotes cell division, also alternatively known as mitosis, replication, multiplication or proliferation.

Cytotrophoblast cells have another receptor type that binds IGF-II very well, binds IGF-I extremely poorly and does not bind insulin. This receptor has been called the type-2 IGF receptor (Rebourcet et al. 1998). This receptor also binds certain glycoproteins that contain mannose-6-phosphate and has also been called the cation-independent mannose-6-phosphate (CIM6P) receptor. We have discovered that competition between IGF-II and latent TGF for binding to the CIM6P/type-2 IGF receptor underlies the action of IGF-II in regulating the ability of cytotrophoblasts to undergo migratory or non-migratory behaviours in any environment.

In the human placenta, IGF-II is most abundantly produced by cytotrophoblast cells that have migrated furthest into the maternal decidual endometrium (Guidice et al. 1998; Irwin et al. 1999). IGF-II promotes migration of cytotrophoblast cells by a mechanism that has hitherto been unknown (Hamilton et al. 1998).

Cytotrophoblast cells have TGF receptors able to bind TGF (Schilling & Yeh 2000). Treatment of cytotrophoblast cells with TGF promotes their fusion to form non-migratory multinucleate giant cells (Morrish et al. 1998).

Active TGF, capable of binding to TGF receptors, is derived by proteolytic conversion from inactive latent TGF, which does not bind to TGF receptors. Latent TGF is produced by maternal uterine decidual cells and by cytotrophoblast cells (Graham & Lala 1991).

Latent TGF is known to bind to the CIM6P receptor. Latent TGF can also bind to CIM6P receptors that are associated in a complex with plasminogen and urokinase plasminogen activator (uPA) receptors.

It is known that uPA converts latent TGF into active TGF by the catalytic action of uPA when bound to the complex formed by the simultaneous association of uPA receptor, plasminogen and latent TGF with the CIM6P receptor (Godar et al. 1999). Cytotrophoblast cells are known to have uPA receptors (Floridon et al. 1999). It has been suggested that binding of IGF-II to the CIM6P receptor is a mechanism that removes and degrades IGF-II. The CIM6P receptor competes with the type-1 IGF receptor for IGF-II binding. IGF-II binding to the type-1 IGF receptor promotes cell division and replication. According to the prior art, the CIM6P receptor reduces the amount of IGF-II able to bind to the type-1 IGF receptor and thus reduces the ability of cells to proliferate or replicate in response to IGF-II. Thus, the CIM6P receptor by competing with the type-1 IGF receptor prevents IGF-II from promoting cell replication. According to the prior art, IGF-II binding to the CIM6P receptor does not produce a direct biological response within the cell upon whose surface the CIM6P receptor is located (Odell & Day 1998).

There is an additional body of evidence that shows that activation of latent TGF occurs on CIM6P receptors located on the cell surface and that this is dependent on simultaneous binding of the uPA/plasminogen system (Godar et al. 1999).

However, it has hitherto not been recognised that IGF-II and latent TGF compete for binding at the same site on CIM6P receptors and that their competition for binding regulates the amount of active TGF formed by this receptor complex and therefore the amount of active TGF available to its specific receptors on the cytotrophoblast cell surface. We have discovered that competition between IGF-II and latent TGF for the CIM6P receptor occurs and that IGF-II inhibits activation of latent TGF and that this is therefore a mechanism for the regulation of cytotrophoblast differentiation and migration. Inhibition of TGF signalling has been shown to promote differentiation of embryonic stem cells into neural stem cells (Tropepe et al. 2001). Therefore alteration of the concentration of IGF-II in the local environment of stem cells will control how much latent TGF is activated and therefore will determine whether these cells differentiate along an epithelial (decreased IGF-II) or mesenchymal or migratory (increased IGF-II) pathway.

DESCRIPTION OF THE PREFERRED EMBODIMENT

Figure 1:
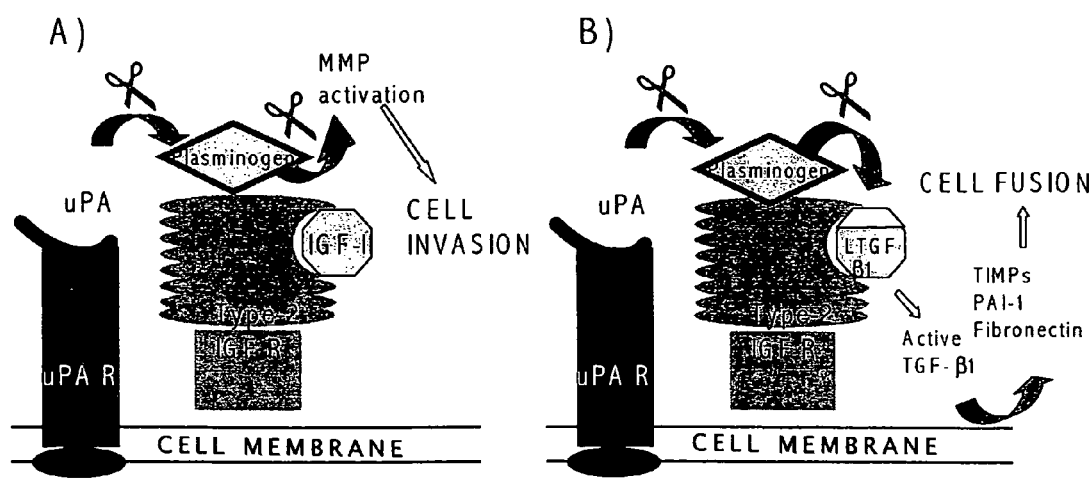
FIG. 1 shows schematically the mechanism by which IGF-II binding to the CIM6P receptor permits cytotrophoblast invasion of the decidua.

The discovery of the interaction of IGF-II and TGF with the CIM6P receptor can be applied by the use of IGF-II in early pregnancy to treat both implantation failure and recurrent spontaneous miscarriage.

During pregnancy cytotrophoblast cells that are originally derived from the trophectoderm of the blastocyst and which subsequently form the placenta remodel the endometrium. The placenta is the active interface between maternal and fetal tissues and is the organ through which exchange of soluble materials between fetus and mother occurs.

The embryo establishes its attachment with the endometrium through the actions of migratory cytotrophoblast cells known as extravillous cytotrophoblasts. They secrete metalloproteinases that degrade the extracellular matrix of the endometrium, permitting their invasion. These invasive cells modify the endometrial spiral arterioles to provide access for the placenta to the maternal blood supply, the source of all matter for embryonic and fetal growth. Cytotrophoblast cells form columns that extend deep into the endometrium. The first wave of invasion of the endometrium by cytotrophoblast cells occurs between 6 and 12 weeks of pregnancy in humans (Pijnenborg et al. 1983). This is the period when most miscarriages occur. It is also the period in which there is no maternal blood flow into the placenta such that cytotrophoblasts proliferate and differentiate in a hypoxic environment. IGF-II is abundantly produced early in pregnancy by cytotrophoblast cells at the leading edge of the invasive front of the cell column. IGF-II promotes the invasive behaviour of cytotrophoblast cells. Latent TGF is produced by decidual cells of the maternal endometrium as well as by cytotrophoblast cells. TGF promotes fusion of cytotrophoblast cells, an essential step in their differentiation to form mature components of the placenta (Morrish et al. 1998). TGF also induces synthesis and secretion of tissue inhibitors of metalloproteinases (TIMPs) by cytotrophoblast cells (Lala & Graham 1990), thus preventing cytotrophoblast cells from degrading the extracellular matrix necessary for their migration.

We hypothesise that early pregnancy loss due to failure to establish a viable placenta is caused by IGF-II deficiency in the IGF-II/TGF/CIM6P receptor system of cytotrophoblasts. Further, it appears that failure of the embryo to successfully implant into the uterine endometrium of the mother is due to insufficient production of IGF-II by cytotrophoblast cells derived from the trophectoderm of the blastocyst, leading to reduced autocrine stimulation of invasion of the endometrium by cytotrophoblast cells. Thus, removal or lack of IGF-II induces terminal differentiation and fusion of cytotrophoblasts.

Spontaneous miscarriage (diagnosed between the 6th and 12th weeks of pregnancy) may thus be caused by deficiency in IGF-II production of cytotrophoblast cells leading to premature fusion before sufficient colonisation of the endometrial decidua has been achieved to establish a healthy placenta. Accordingly, IGF-II can be used to treat both implantation failure and recurrent spontaneous miscarriage.

Impaired cytotrophoblast invasion of the uterine decidua is associated with pre-eclampsia, a common hypertensive disorder of pregnancy which is life-threatening in 3% of pregnancies in developed nations. It follows that deficiency of IGF-II synthesis by extravillous cytotrophoblasts results in reduced invasive behaviour, poor placentation and pre-eclampsia. TGF has also been associated with pre-eclampsia as women who develop this disease have elevated concentrations of active TGF 1 in their blood (Djurovic et al. 1997). We claim that this is a result of insufficient IGF-II to maintain activation of TGF at normal levels.

We have discovered that IGF-II and latent TGF, the precursor of TGF, compete for binding to CIM6P receptors in human placenta. Latent TGF binding to CIM6P receptor is known to lead to its proteolytic conversion by plasmin into active TGF by the complex formed between urokinase plasminogen activator (uPA), uPA receptor and plasminogen (Godar et al. 1999). It is known that cytotrophoblast cells have CIM6P receptors (Rebourcet et al. 1998) and uPA receptors (Floridon et al. 1999). It follows from our discovery that secretion of IGF-II by cytotrophoblast cells maintains their invasive state by preventing local activation of TGF, the initiator of their terminal differentiation into non-replicating and non-migratory cells. It is known that invasive cytotrophoblast cells produce IGF-II in abundance (Irwin et al. 1999).

We show herein that IGF-II and latent TGF compete for binding to the placental CIM6P receptor. It is known that activation of TGF from its latent form is a prerequisite for its promotion of cytotrophoblast cell fusion and terminal differentiation. It has been discovered that IGF-II inhibits terminal differentiation of cytotrophoblast cells and, that this is the means by which IGF-II promotes cytotrophoblast cell invasion of the decidua.

In FIG. 1 the mechanism by which IGF-II promotes cytotrophoblast invasion of the decidua is shown. In (A) IGF-II inhibits binding of latent TGF to the receptor and permits the simultaneous activation of matrix metalloproteinases by plasmin produced by the action of uPA on plasminogen secreted by cytotrophoblasts to facilitate their migration into the uterine decidua. (B) When latent TGF binds the CIM6P receptor, plasmin that is generated as above is available to cleave the latency associated peptide from latent TGF resulting in activation of TGF which may then bind its specific receptors at the cell surface and induce cytotrophoblast terminal differentiation.

In accordance with our discovery that IGF-II and TGFβ compete for CIM6P binding, we have also discovered that during placental development, CIM6P receptor-bound IGF-II maintains cytotrophoblast cell type and promotes degradation of extracellular matrix essential for invasion of the endometrium by cytotrophoblast cells. Binding of latent TGF to the same CIM6P receptor, in preference to IGF-II, activates TGF which initiates cytotrophoblast differentiation into a non-migratory cell type and promotes fusion into multinucleate placental bed giant cells. Thus, it is suggested that early pregnancy loss is characterised by inadequate IGF-II synthesis or premature reduction or cessation of IGF-II synthesis and secretion by extravillous cytotrophoblast cells, which allows binding of latent TGF to their CIM6P receptors. Deficiency in IGF-II results in premature activation of TGF by the uPA system complexed to the CIM6P receptor. We claim that premature activation of TGF is a consequence of IGF-II deficiency in cytotrophoblast cells. Active TGF then promotes premature fusion of cytotrophoblast cells. This reduces the numbers of invading extravillous cytotrophoblast cells below critical levels required to form a placenta that can sustain adequate extraction of oxygen and nutrients from the utero-placental blood supply for use by the placenta and the embryo and fetus. The placenta necroses and miscarriage ensues. We claim that IGF-II delivered to the implantation site promotes extravillous cytotrophoblast cell invasion.

As normal pregnancy advances, cytotrophoblast cells become progressively exposed to increasing amounts of both oxygen and maternal adrenal glucocorticoids. It is known that both oxygen and glucocorticoids inhibit production of IGF-II by many cell types. This allows more latent TGF to bind to the CIM6P receptor and therefore increases the amount of active TGF produced at the cell surface. Increased exposure to active TGF causes terminal differentiation of cytotrophoblasts into non-replicating, non-invasive cells. The timing of premature terminal differentiation of cytotrophoblasts determines the severity of the defect in implantation and placentation.

Up to 50% of miscarriages have been attributed to inadequate invasion of the decidua by cytotrophoblast cells (Khong et al. 1987). We claim that reduced IGF-II production by cytotrophoblast cells during embryo implantation and in the first weeks of pregnancy causes implantation failure and miscarriage.

Pre-eclampsia, a hypertensive disorder that occurs later in pregnancy and is also characterised by impaired cytotrophoblast cell invasion of the decidua (Khong et al. 1986), is, according to our discovery, caused by IGF-II deficiency of cytotrophoblast cells. The effects of impaired cytotrophoblast invasion in the first trimester of pregnancy are not apparent symptomatically in the mother until later. The most severe form of pre-eclampsia is diagnosed during the middle trimester of pregnancy, while less severe cases are not diagnosed until later in the third trimester. We claim that the more severe forms of pre-eclampsia are characterised by a poor capacity of cytotrophoblast cells to synthesise IGF-II and a poor response of these cells to synthesise IGF-II in hypoxic conditions as occur in the first trimester of pregnancy. Less severe forms of pre-eclampsia are also due to inadequate cytotrophoblast production of IGF-II but their IGF-II response to hypoxia is between that in severe cases and normal pregnancy.

A diagnostic test based on cytotrophoblast capacity for IGF-II synthesis conducted early in pregnancy to identify those at risk of symptoms of pre-eclampsia later in pregnancy would allow early treatment and monitoring by health care providers. It is our discovery that IGF-II can be used to prevent and treat pre-eclampsia by elevating circulating IGF-II concentrations to the normal pregnancy range which has been previously shown to be about 2,200 ng/ml in pooled serum compared to about 1500-1600 ng/ml in the non-pregnant state (Gargosky et al. 1990).

Convenient methods of treatment with IGF-II would include the use of subcutaneous delivery devices or extended release vaginal pessaries. A range of other conventional delivery systems would be suitable. Treatment with IGF-II is concerned with raising the maternal blood level of IGF-II to 'normal' levels throughout the pregnancy, that is the treatment is a generally remedial action preferably to be applied in situations where diagnosis has indicated a predicted or measured reduction in IGF-II levels. The duration of treatment will therefore be specific to each individual concerned. In some cases the treatment may be continued throughout the pregnancy and in other treatment may be required only during the first half of the pregnancy.

A less severe form of impaired cytotrophoblast cell invasion leads to placental abruption (Dommisse & Tiltman, 1992), in which premature separation of the placenta from the decidua occurs in the last weeks of pregnancy, and which requires emergency delivery of the baby, is also due to moderate IGF-II deficiency of cytotrophoblast cells. IGF-II can be used to prevent placental abruption.

IGF-II deficiency impairs the ability of cytotrophoblast cells to invade the decidua. The diseases of pregnancy discussed above form a continuum of related disorders that depend on the degree of IGF-II deficiency and consequently the timing and extent of the reduced invasion of the decidual endometrium by cytotrophoblast cells.

EXAMPLE 1

IGF-II competes with latent TGF for binding to cation-independent mannose-6-phosphate receptors on human placental microsomal membranes The competition between IGF-II and latent TGF for the CIM6P binding site can be demonstrated as follows:

Human placenta was obtained from the Women's and Children's Hospital, North Adelaide after delivery of a normal baby following an uncomplicated pregnancy, and used as a source of CIM6P receptors (Owens et al. 1980). A suspension of microsomal membranes was prepared from the placenta by homogenisation and differential ultra-centrifugation (Owens et al. 1980). Human IGF-II and IGF-I (receptor grade) were obtained from GroPep Pty. Ltd. Human latent TGF 1 was purchased from R&D Systems, Inc. IGF-II was radioactively labelled with iodine-125 to a specific activity of 70 Ci/g using chloramine-T (Francis et al. 1989). IGF-II labelled in this manner does not bind to type-1 IGF receptors (Francis et al. 1989). Replicates of 10 g of human placental microsomal protein were simultaneously incubated at 4° C. for 20 h in 150 l of 0.05 mol/litre Tris-HCl buffer pH 7.4 containing 1 picomole of iodo-125-IGF-II, 0.01 mol/litre calcium chloride and 5 gram/litre bovine albumin (Owens et al. 1985). Different replicates also contained either IGF-II, IGF-I or latent TGF 1 at a number of different concentrations. Radioactivity bound to human placental microsomal membranes was recovered by centrifugation (Owens et al. 1985). Blank binding of iodo-125-IGF-II was measured in the absence of human placental microsomes. Non-specific binding of iodo-125-IGF-II was measured in the presence of unlabelled IGF-II at a concentration of 133 nanomol/litre (Owens et al. 1985).

IGF-I, IGF-II and latent TGF 1 inhibited the binding of iodo-125-IGF-II to human placental microsomes (Table 1).

Unlabelled IGF-II when present at a concentration of 1.6 nanomol/litre inhibited specific binding of iodo-125-IGF-II by 40% and by 87% when present at a concentration of 15 nanomol/litre. Unlabelled IGF-I at a concentration of 1,600 nanomol/litre inhibited the specific binding of iodo-125-IGF-II by 68%. Unlabelled latent TGF 1 inhibited specific binding of iodo-125-IGF-II by 25% when present at a concentration of 115 nanomol/litre (Table 1).

TABLE 1

Effects of unlabelled insulin-like growth factors and unlabelled latent transforming growth factor on binding of radioactively labelled insulin-like growth factor II to human placental microsomal membranes.

| | |
|---|---|
| Radioactivity added | 40,709 counts per minute (cpm) |
| Total radioactivity bound | 7,733 cpm (19.0% of the radioactivity added) |
| Blank radioactivity bound | 2,606 cpm (6.4% of the radioactivity added) |
| Radioactivity bound non-specifically | 3,558 cpm (8.7% of the radioactivity added) |
| Radioactivity bound specifically | = 7,733 cpm − 3,588 cpm |
| | = 4,145 cpm |
| | = 10.2% of the radioactivity added |
| | = 53.6% of the total radioactivity bound |
| Radioactivity bound in the presence of the following: | |
| unlabelled IGF-II at 1.6 nanomol/liter | 6,059 cpm |
| unlabelled IGF-II at 15 nanomol/liter | 4,120 cpm |
| unlabelled IGF-I at 1,600 nanomol/liter | 4,905 cpm |
| unlabelled latent TGF 1 at 116 nanomol/liter | 6,717 cpm |

*Radioactivity bound specifically is calculated to be the arithmetic difference between the total radioactivity bound and the radioactivity bound non-specifically.

Example 1 demonstrates that latent TGF 1 and iodo-125-IGF-II compete for binding to the same site in suspended microsomal membranes prepared from human placenta. IGF-II also inhibits binding of iodo-125-IGF-II to the same cell membranes.

The specific binding of iodo-125-IGF-II to human placental microsomes in this example is not due to binding to either insulin receptors or type-1 IGF receptors, because more than 100-times more unlabelled IGF-I is required to inhibit binding of iodo-125-IGF-II by as much as achieved by unlabelled IGF-II (Table 1). It is known that IGF-I and IGF-II have similar affinities for their binding of both insulin receptors and type-1 IGF receptors. It is known that IGF-I has a very poor affinity for binding the CIM6P receptor.

The example above demonstrates that iodo-125-IGF-II binds to CIM6P receptors in human placenta and that latent TGF 1 inhibits this binding. Accordingly, latent TGF and IGF-II compete for binding to CIM6P receptors.

Example 2

IGF-II Inhibits Activation of Latent TGF

Figure 2:
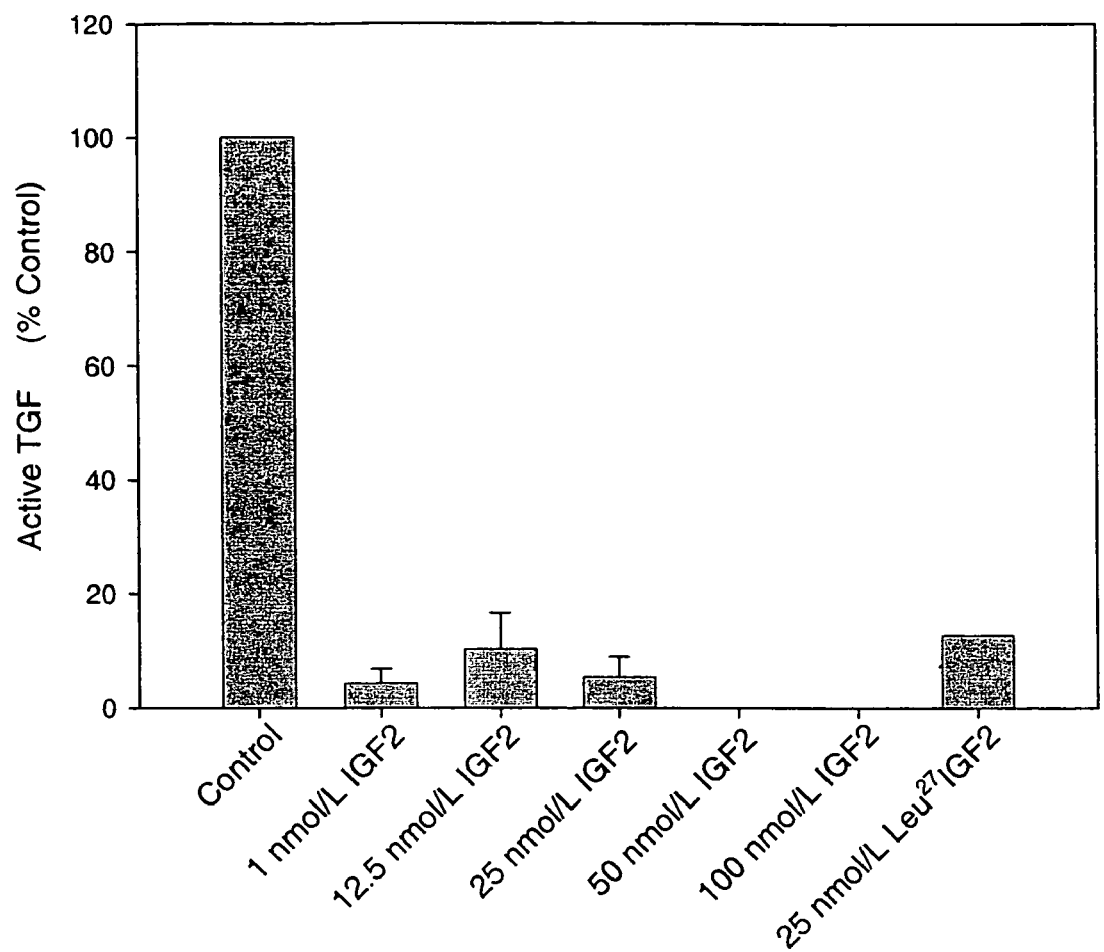
FIG. 2 illustrates the effect of IGFs on activation of TGF by human TF1 monocytes.

The result of competition between IGF-II and latent TGF for the CIM6P binding site and its effect on activation of latent TGF can be demonstrated as follows:

Human TF1 cells, a monocyte cell line, which express essential components of this system described above ie. CIM6P receptors, urokinase plasminogen activator receptors and secrete abundant latent TGF 1 into the culture media, were cultured in serum-free RPMI 1640 media (JRH Biosciences) with 2% serum replacement (Sigma), $3.5 \times 10^{-6}$%-mercaptoethanol (Sigma), 4 mM l-glutamine (CSL), 10 g/ml plasminogen (Sigma), 5 g/ml urokinase plasminogen activator (uPA) (Sigma) and 2 ng/ml recombinant human granulocyte-macrophage colony stimulating factor (GM-CSF) (Leucomax, Schering-Plough). In replicate wells, monocytes were incubated with either 0, 1, 12.5, 25, 50 or 100 nM receptor grade IGF-II or 25 nM receptor grade Leu$^{27}$IGF-II (GroPep, Adelaide). Approximately $1-2 \times 10^6$ monocytes were placed in 500 l media and cultured for 24-26 hours at 37 C in 20% oxygen, 5% carbon dioxide, 75% nitrogen. The cell suspension was then gently aspirated and spun in a centrifuge at 200 g for 10 mins at room temperature. The supernatant was collected and frozen at −20 C until assay for active and total TGF-1. Cells were resuspended in Hank's Balanced Salt Solution (HBSS, JRH Biosciences) and counted to determine the effect of culture on cell proliferation. Supernatants were thawed and assayed for TGF-1 using a commercially available human TGF-1 enzyme-linked immunosorbent assay (ELISA) kit (R&D Systems, Inc.) according to the manufacturer's instructions. Color development was quantified using a BioRad Benchmark microplate reader set at a wavelength of 450 nm and corrected to 550 nm. The concentration of TGF-1 was calculated automatically by comparing with a standard curve of known concentrations of TGF on the same microplate using BioRad Microplate Manager 5.0 PC Software. Active and total TGF-1 were then calculated per million cells at the end of the culture period. The following table of results, table 2, shows that TF1 monocytes secrete abundant latent TGF-1 into the culture medium and that IGF-II inhibits activation of latent TGF-1. This is shown graphically in FIG. 2. When uPA is omitted from the culture media there is no activation of latent TGF-1. This provides further evidence that it is the uPA/uPAR/CIM6P receptor system which is responsible for activation of latent TGF on the cell surface.

TABLE 2

The effect of IGF-II on activation of latent TGF by $1 \times 10^6$ TF1 monocytes in vitro.

| IGF-II or Leu$^{27}$-IGF-II Concentration | Total TGF −1 (pg/ml) | | Active TGF −1 as % Control | |
|---|---|---|---|---|
| 0 nmol/L IGF-II | 238.49 | 33.09 | 100.0 | |
| 1 nmol/L IGF-II | 229.73 | 6.33 | 4.25 | 2.60 |
| 12.5 nmol/L IGF-II | 252.67 | 10.41 | 10.28 | 6.33 |
| 25 nmol/L IGF-II | 274.70 | 25.13 | 5.37 | 3.55 |
| 50 nmol/L IGF-II | 335.95 | | 0.00 | |
| 100 nmol/L IGF-II | 321.08 | | 0.00 | |
| 25 nmol/L Leu$^{27}$-IGF-II | 366.64 | | 12.72 | |

All data is Mean SEM

Hence, we have shown that IGF-II inhibits the activation of latent TGF in vitro.

Example 3

Effect of Oxygen on Cytotrophoblast Column Formation In Vitro

It is known that binding of latent TGF to CIM6P receptors present on monocytes that also have uPA receptors results in proteolytic conversion of latent TGF into active TGF (Godar et al. 1999). It is known that cytotrophoblast cells have CIM6P receptors (Rebourcet et al. 1998) and uPA receptors (Floridon et al. 1999). TGF is known to change cytotrophoblast cells from the invasive type to the fused, terminally differentiated type resulting in formation of multinucleate trophoblast cells called placental bed giant cells. It therefore follows that IGF-II inhibits activation of latent TGF by cytotrophoblast cells by preventing latent TGF from binding to CIM6P receptors of cytotrophoblast cells.

We also show herein that during early human pregnancy (7.5-8 weeks) when placentation is being established and cytotrophoblasts are known to be exposed to low oxygen tensions, they are most invasive and both IGF-II protein and mRNA expression is increased. The effect of oxygen on IGF-II mRNA expression and the association of IGF-II mRNA with extravillous cytotrophoblast column formation can be demonstrated thus:

Human first trimester placentas were obtained from the Women's and Children's Hospital, North Adelaide, from legal elective terminations of normal pregnancies of 7.5-8 weeks gestation. Placental villous tissue was obtained immediately after vaginal curettage. Villous tissue was washed to remove blood, using cold, sterile PBS, then transported to the laboratory on ice, in HEPES buffered DMEM/F12 supplemented with 10% heat-inactivated fetal bovine serum (HIFBS) and 40 ng/ml gentamycin (GIBCO BRL, Grand Island, N.Y.). The tissue was then rinsed and dissected into 2-3 mm pieces in villous culture media (described below) at 37° C., under aseptic conditions.

Villous culture media consisted of DMEM/F12 (GIBCO BRL, Grand Island, N.Y.) supplemented with: 0.04 mM 1-glutamine; 20 ng/ml plasminogen; 20 I/ml antibiotic mix (GIBCO BRL, Grand Island, N.Y.), comprised of 200 units/ml penicillin, 200 g/ml streptomycin and 0.5 g/ml amphotericin; with 10% HIFBS (CSL, Parkville, Vic).

Falcon 24-well tissue culture plates (Becton Dickinson, Kranklin Lakes, N.J.) were coated with 20 l of 1:1 Matrigel: culture media (Matrigel from GIBCO BRL, Grand Island, N.Y.), set in a humid incubator at 37° C. for at least 30 minutes. Villous pieces were weighed, one piece carefully plated per well, and covered with 15 l of 1:1 Matrigel:culture media. The Matrigel was set in an incubator for 20 minutes, before 400 l of culture media was added and the explants cultured overnight, at 37° C. in 5% $CO_2$ and either 20% or 1% $O_2$ (equivalent to 98 mmHg or 7-10 mmHg).

The following morning (≈15 hours), by which time villous tips were adherent to the bottom of the well, 600 l of culture media was added per well, and explants were returned to the same culture conditions. Cultures were maintained for 6-8 days, with media changed every second day.

Villous cultures were digitally photographed (on an Olympus DP12 camera) immediately before RNA extraction was performed. From these photographs, cytotrophoblast outgrowths were visually scored for their pattern of outgrowth. Absolute counts were recorded for: 1) number of adherent villous tips with outgrowth and 2) number of cell column formations. The number of cell columns per explant were then divided by the total number of tips with outgrowth for that explant.

TRIZOL (GIBCO BRL, Grand Island, N.Y.) was used to extract RNA from villous cultures, according to the manufacturer's protocol for cells grown in a monolayer. For placental villous cultures, 300 l TRIZOL per well was used. RNA concentration was determined by measuring UV light absorbance at 260 nm on a DU-50 Spectrophotometer (Beckman Instruments, Irvine, Calif.).

Aliquots containing 2 g of RNA from each sample were reverse transcribed. The RNA was incubated with random hexamer primers at 65° C. for 10 minutes. Tubes were cooled on ice for 5 minutes and ExpandRT, 5× buffer, DTTs (Roche Diagnostics, Indianapolis, Ind.), and Ultrapure dNTPs (Amersham Pharmacia Biotech, Piscataway, N.J.) were added, according to the manufacturer's instructions. The tubes were then incubated at 30° C. for 5 minutes, 42° C. for 45 minutes, and 95° C. for 2 minutes, cooled on ice and the cDNA was stored at −20° C.

Using PrimerExpress software (Applied Biolsystems, Foster City, Calif.). IGF-II oligonucleotide primers were designed to span exons 3 and 4 of the human IGF-II gene (GenBank accession number X03562), giving a predicted amplicon of 90-100 bp. Primers were: forward, 5'-CCC CTC CGA CCG TGC T-3' [SEQ ID NO: 1]; reverse, 5'-TGG ATG GAC TGC TTC CAG GTG TCA T-3' [SEQ ID NO: 2]. Standard purity primers were made by GensetOligos (Genset Pacific, Lismore, Australia).

Aliquots of 2 l of cDNA were amplified in a reaction mixture (20 l) containing 1 µl of each IGF-II primer at 10 M/l, 10 l of SYBR Green Master Mix (including AmpliTaq® Gold DNA Polymerase, Applied Biosystems, Foster City, Calif.) and 6 l of molecular grade water (Fluka BioChemika, Messerschmittstr, Germany). For the 18s rRNA endogenous control, 2 l of a 1/10 cDNA dilution was amplified in a reaction mixture (20 l) containing 2 l of Universal 18s primer pair mix (Ambion, Austin, Tex.), 10 l of SYBR Green Master Mix and 7 l of molecular grade water. Three replicates of each cDNA sample were amplified, and negative controls in which cDNA was omitted (water substituted) were included to test for contamination.

Using a GeneAmp 5700 thermal cycler (Applied Biosystems, Foster City, Calif.), the samples were amplified in 1 cycle of 50° C. for 2 minutes, 95° C. for 10 minutes, followed by 40 cycles of 95° C. for 15 seconds and 60° C. for 1 minute. The critical threshold ($C_T$) value for each sample was determined with the fluorescence threshold set at 0.150 runs.

Aliquots of 7 l of PCR product were fractionated by electrophoresis, in parallel with pUC19 molecular weight markers, in a 2% agarose gel (Sigma Chemical Co, St Louis, Mo.), stained with ethidium bromide. Bands were visualised under UV light, and digitally photographed.

Figure 3:
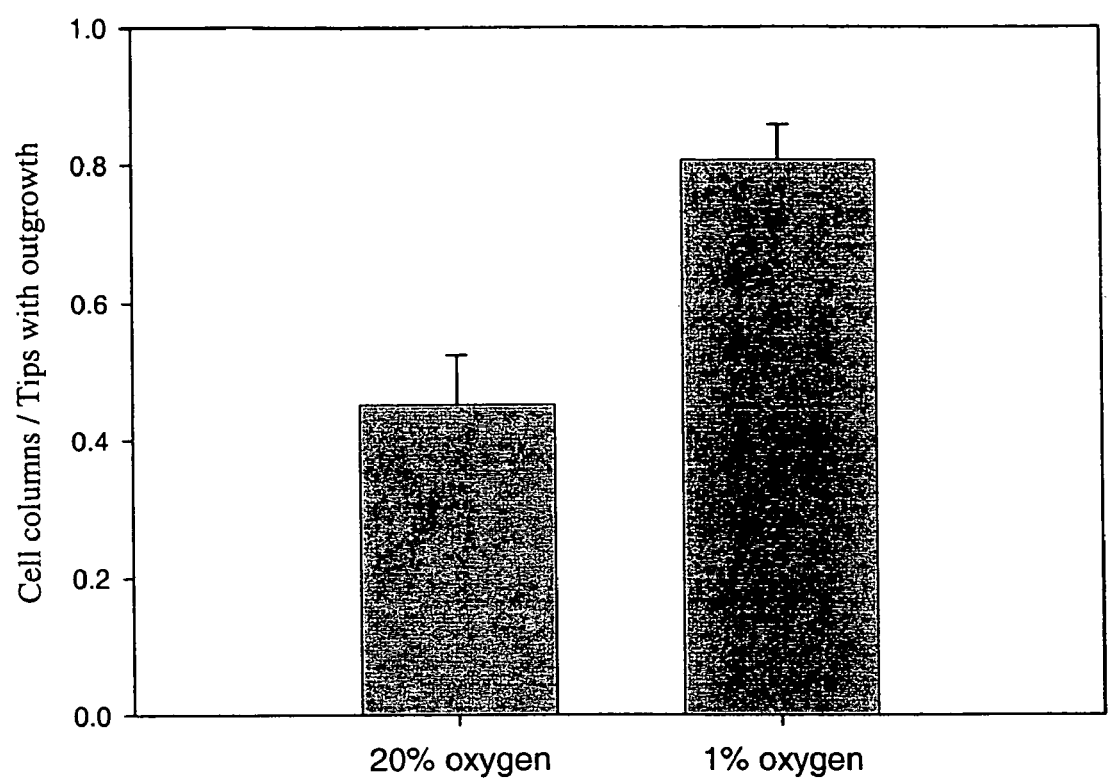
FIG. 3 illustrates the effect of oxygen on the number of outgrowing tips from human placental villous explants which formed cytotrophoblast cell columns.

FIG. 3 shows graphically that the number of cytotrophoblast cell columns per growing placental villous tip is increased by culture in hypoxic conditions.

Figure 4:
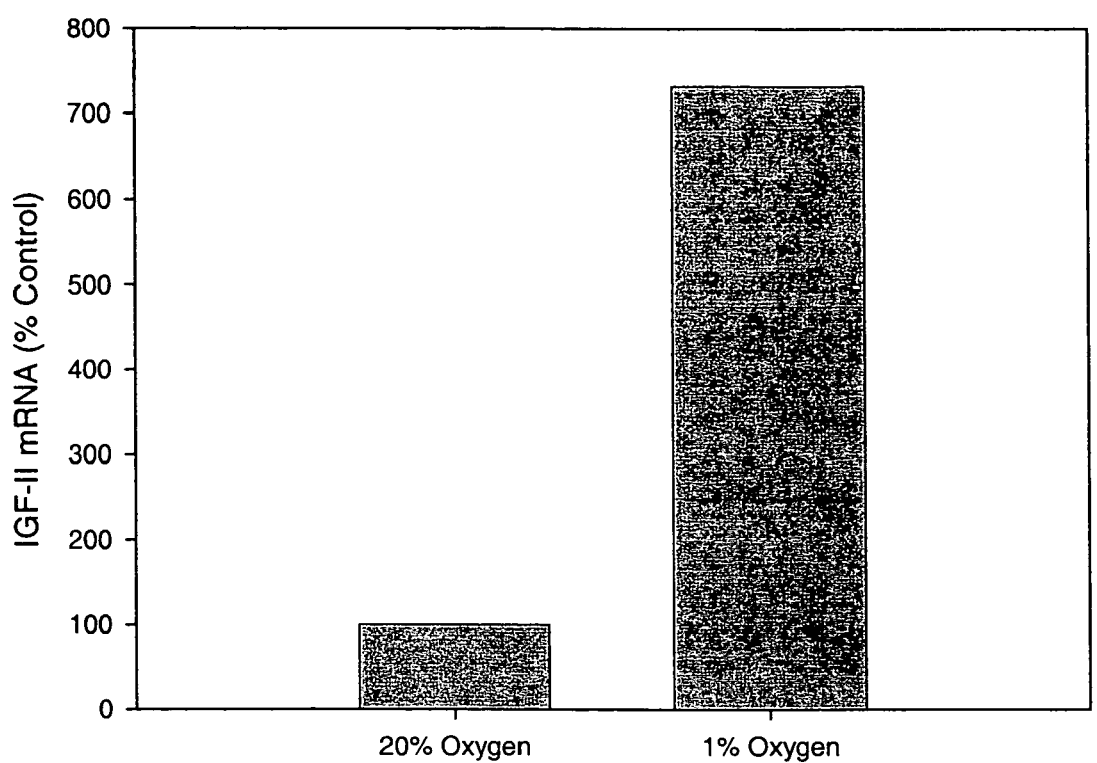
FIG. 4 illustrates the effect of oxygen on IGF-II mRNA expression by human placental villous explants at 7.5-8 weeks gestation.

FIG. 4 shows graphically the ranked CT medians were transformed to show IGF-II mRNA expression for each treatment group relative to the median for the calibrator (control) group for the hypothesis being tested, given as 100%.

Thus exposure of extravillous explants to hypoxic culture conditions increases the number of cytotrophoblast cell columns and increases extravillous cytotrophoblast invasive behaviour. In addition, culture in 1% oxygen induces a 7-fold increase in IGF-II mRNA synthesis in placentas of 7-8.5 weeks which will greatly increase their capacity for invasion of the uterine decidua and subsequent placental differentiation. IGF-II mRNA was positively correlated with the proportion of outgrowing villous tips that formed cytotrophoblast cell columns ($r=-0.296$, $n=65$, $p=0.017$).

Treatment with IGF-II thus promotes and maintains the invasive state of cytotrophoblast cells by inhibiting their fusion due to preventing activation of latent TGF by binding to CIM6P receptors of cytotrophoblast cells. Alternatively, culture in low oxygen conditions (less than 3%) stimulates IGF-II production, thus adjusting the level of IGF-II in the cellular environment to thereby maintain the mesenchymal migratory phenotype.

Example 4

IGF-II Enhances Placental Development In Vivo

Enhanced invasion of cytotrophoblasts during pregnancy results in a more functional placenta because the circumferential expansion of the placenta as it grows, as well as acquisition of an adequate utero-placental blood supply, depend on trophoblast invasion of the decidua. It has previously been shown that in pregnant guinea pigs the concentration of IGF-II in maternal blood during pregnancy is a predictor of the structural development of the placenta, parameters of which correlate with placental function and fetal weight and that this is a particularly strong association in early to mid-gestation when the placenta is in its hyperplastic growth phase (Roberts et al., 2001). Therefore we also show herein the effect of treatment of the pregnant mother with exogenous IGF-II on placental growth and development.

We obtained 30 eight week old C57Bl/6 female mice from the University of Adelaide Medical School Animal House and divided them into three groups of similar weight.

Females were mated with 9-10 week Balb/C male mice and checked for the presence of a vaginal copulatory plug the next morning. The day of the copulatory was designated as day 1 of pregnancy. At midday on day 2 of pregnancy mice were treated with either 0, 12.5 or 25 µg/day IGF-II, which translates to 0, 0.5 or 1.0 mg/kg/day IGF-II based on weight at mating, in 0.1 mmol/L acetic acid delivered by a subcutaneous osmotic minipump (Alzet 1007D) from days 2-10 of pregnancy. Osmotic minipumps were inserted subcutaneously on the back under anaesthesia and strict aseptic conditions. Anaesthesia was induced with 3% halothane in oxygen using an anaesthetic machine and maintained with 2% halothane. The lower back was shaved and swabbed and a 1.0 cm transverse incision was made. An artery clamp was used to make a long subcutaneous pocket higher up on the back such that when the minipump was inserted it lay well away from the incision which was then closed with 2 wound clips. Mice were given one or two puffs of pure oxygen after which they regained consciousness within one minute. Pumps were not primed so as to delay the initiation of pumping by 4-6 hours. Osmotic minipumps delivered 0, 12.5 or 25 µg/day IGF-II, at a flow rate of 0.52 l/h which was equivalent to 0, 0.5 or 1.0 mg/kg/day IGF-II based on body weight at surgery. Mice were killed by ether overdose on day 18 of pregnancy (term=19 days). Blood was taken in heparinized tubes and centrifuged. Plasma was frozen at −20 C. Placentas and fetuses were excised from the uterus and weighed. The mother's carcass minus the uterus and minipump was weighed.

Figure 5:
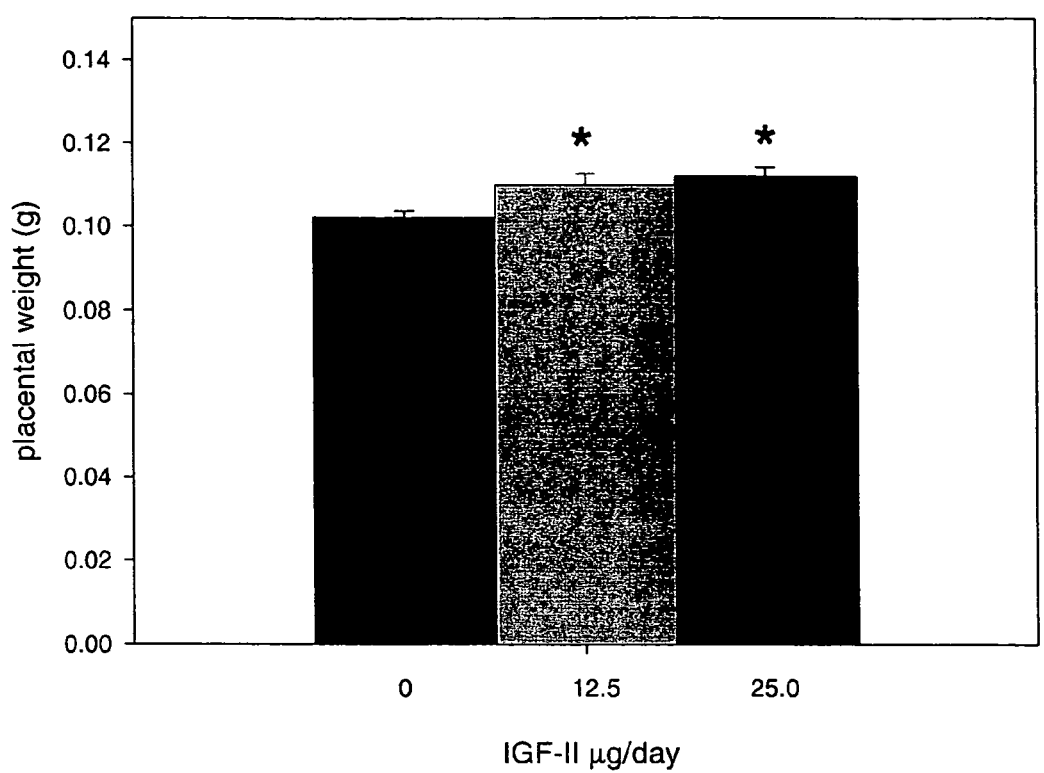
FIG. 5 illustrates the effect of treatment with IGF-II between days 2 and 10 of pregnancy in the mouse on placental weight at day 18.
Figure 6:
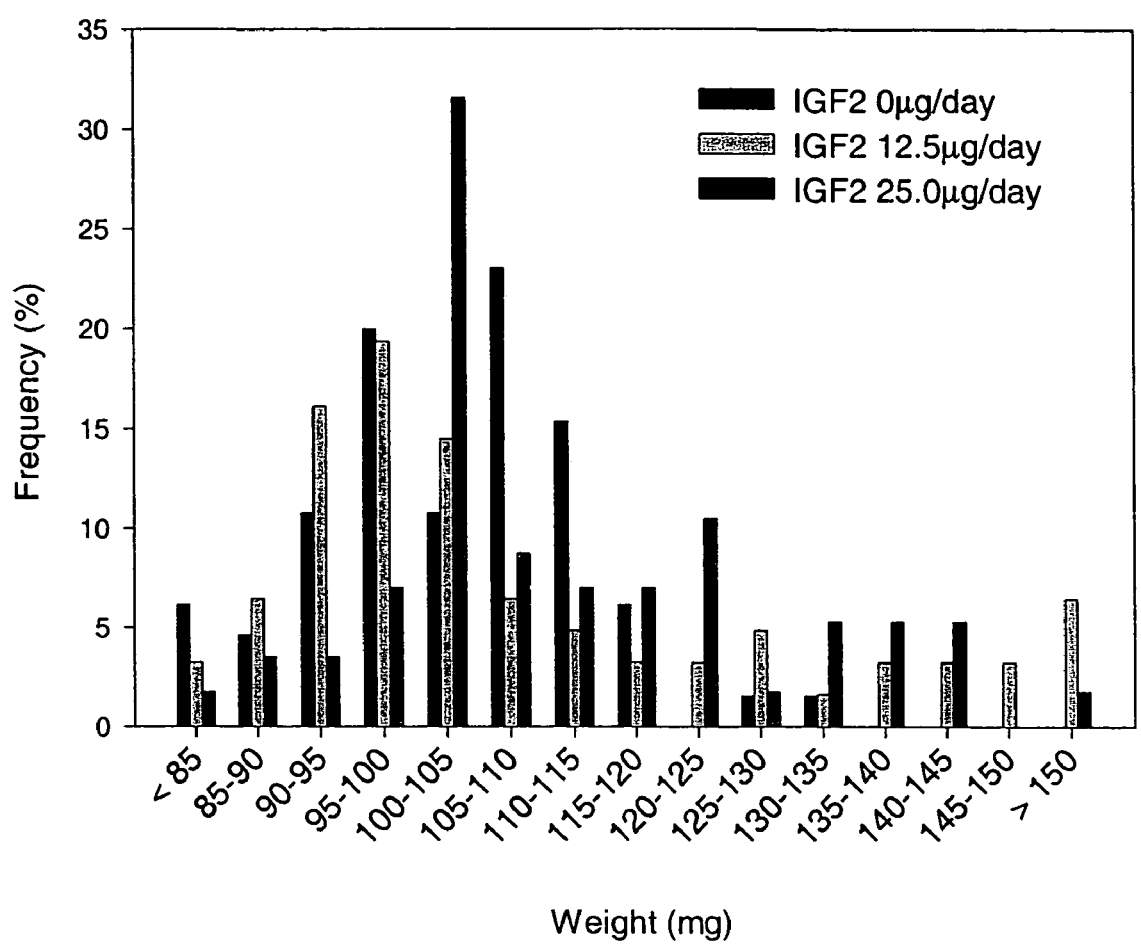
FIG. 6 illustrates the effect of treatment with IGF-II between days 2 and 10 of pregnancy in the mouse on the distribution of placental weights at day 18.

The results, as depicted in FIGS. 5-13 indicate that treatment of pregnant mice between days 2 and 10 of pregnancy increased placental weight at day 18 of gestation by 7.5% (p<0.05) and 9.6% (p<0.05) by treatment with 12.5 or 25 µg/day IGF-II, respectively (FIG. 5). The distribution of placental weights across litters was skewed to the right by treatment with IGF-II. The percentage of placentas that weighed more than 120 mg was 3.1% in control mice, 25.8% in mice treated with the 12.5 µg/day IGF-II, (p<0.0001) and 29.8% in mice treated with the 25 µg/day IGF-II (p<0.0001) (FIG. 6).

Figure 7:
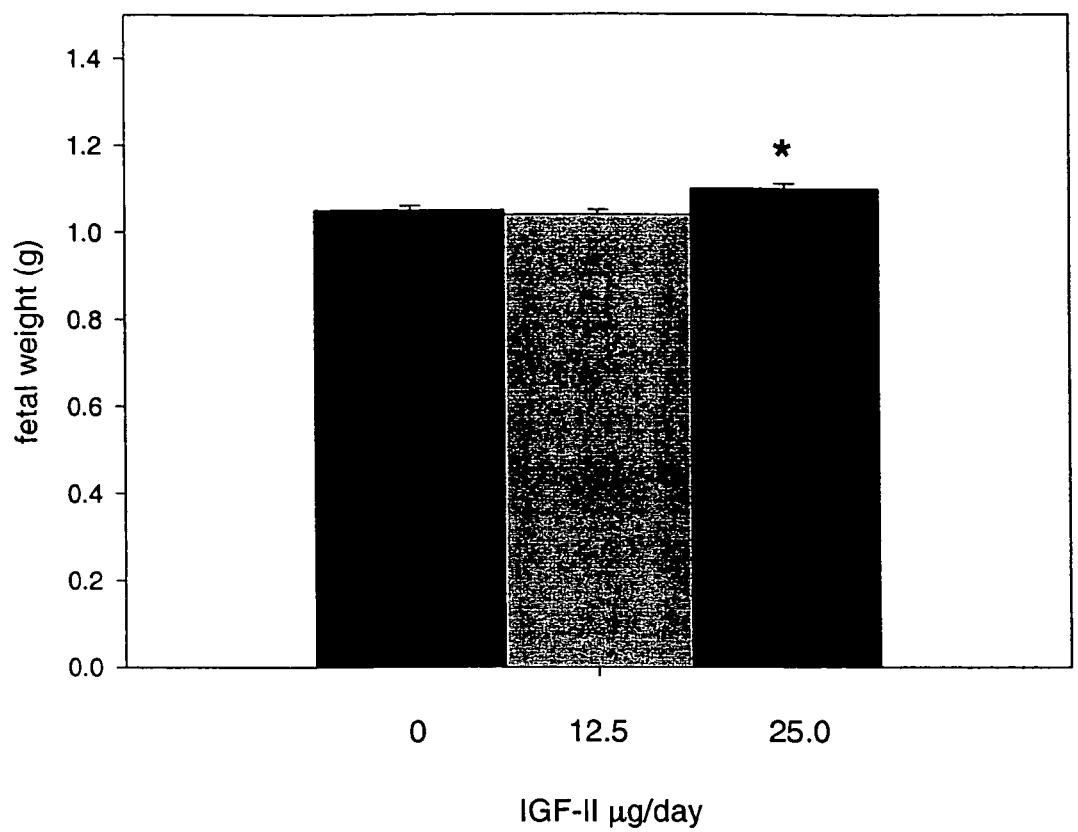
FIG. 7 illustrates the effect of treatment with IGF-II between days 2 and 10 of pregnancy in the mouse on fetal weight at day 18.
Figure 8:
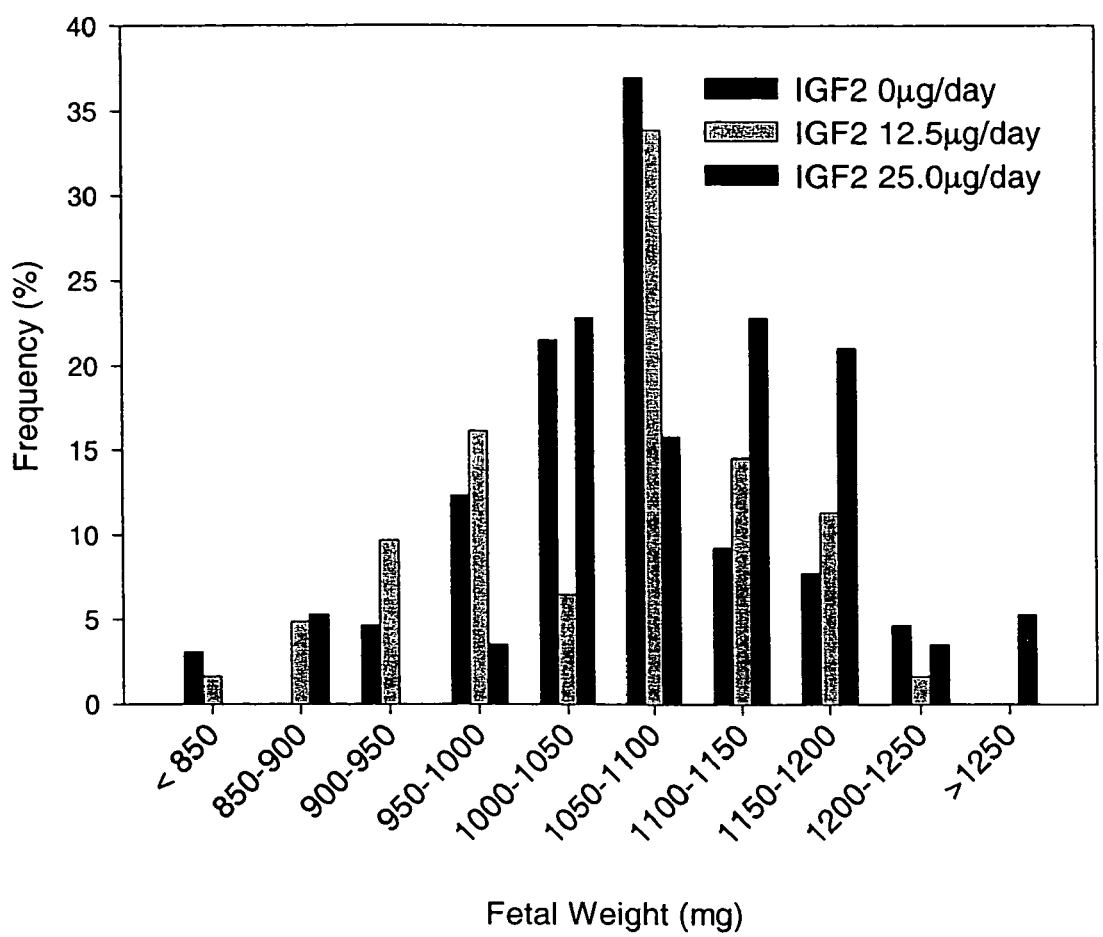
FIG. 8 illustrates the effect of treatment with IGF-II between days 2 and 10 of pregnancy in the mouse on the distribution of fetal weights at day 18.
Figure 9:
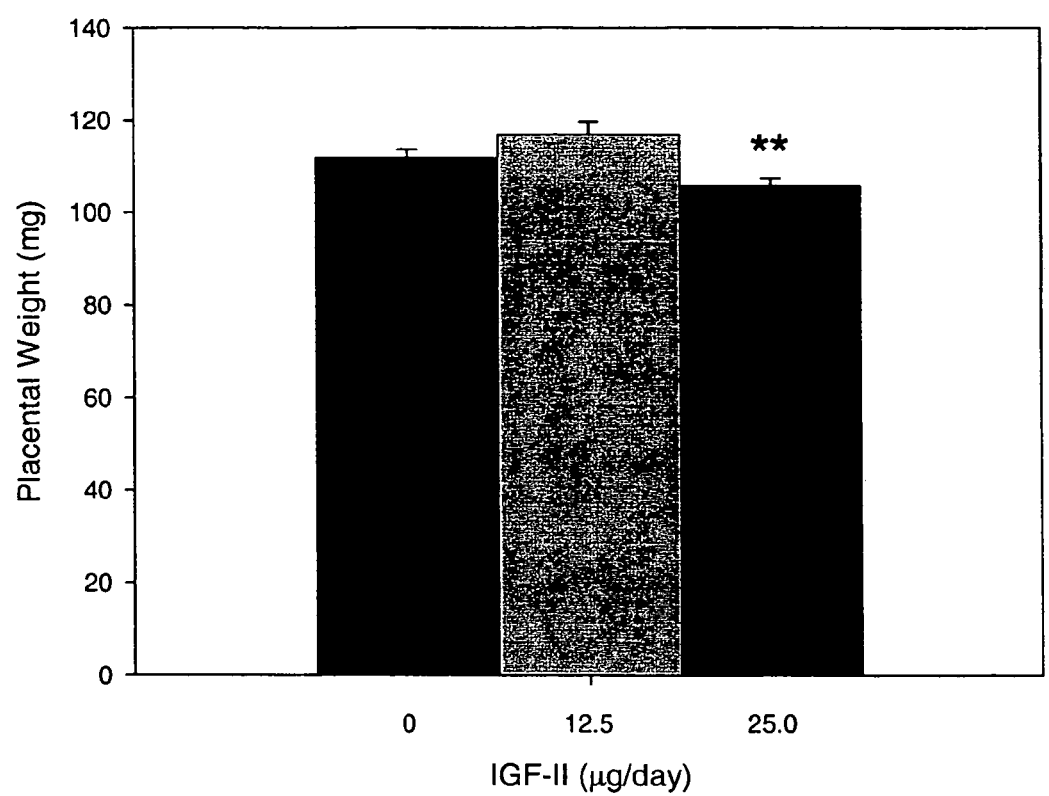
FIG. 9 illustrates the effect of treatment with IGF-II between days 2 and 18 of pregnancy in the mouse on placental weight at day 18.

Thus treatment of the mother with slow release IGF-II during the first half of pregnancy enhances placental growth. Treatment with 25 µg/day IGF-II increased fetal weight by 4.1% (p<0.05) (FIG. 7). The distribution of fetal weights across litters was skewed to the right by treatment with IGF-II. The percentage of fetuses weighing more than 1100 mg was 21.5% in control mice, 27.4% in mice treated with 12.5 µg/day IGF-II (NS) and 53.6% in mice treated with the 25 µg/day IGF-II (p<0.0001) (FIG. 8).

There was no difference in maternal weight gain or net carcass weight following treatment with IGF-II during pregnancy. Maternal weight gain was only related to litter size. This suggests that treatment with IGF-II at these doses does not increase cell proliferation in the mother.

In a second replicate of 30 pregnant mice, treatments were identical to the first replicate except that the osmotic minipumps used (Alzet 1002) delivered the growth factor or vehicle at 0.22 l/h from days 2-18 of pregnancy when the animals were killed and fetal and placental weights recorded. The daily dose delivered was identical to that of the first replicate, either 0, 12.5 or 25 µg/day IGF-II, which translates to 0, 0.5 or 1.0 mg/kg/day IGF-II based on weight at mating.

Figure 10:
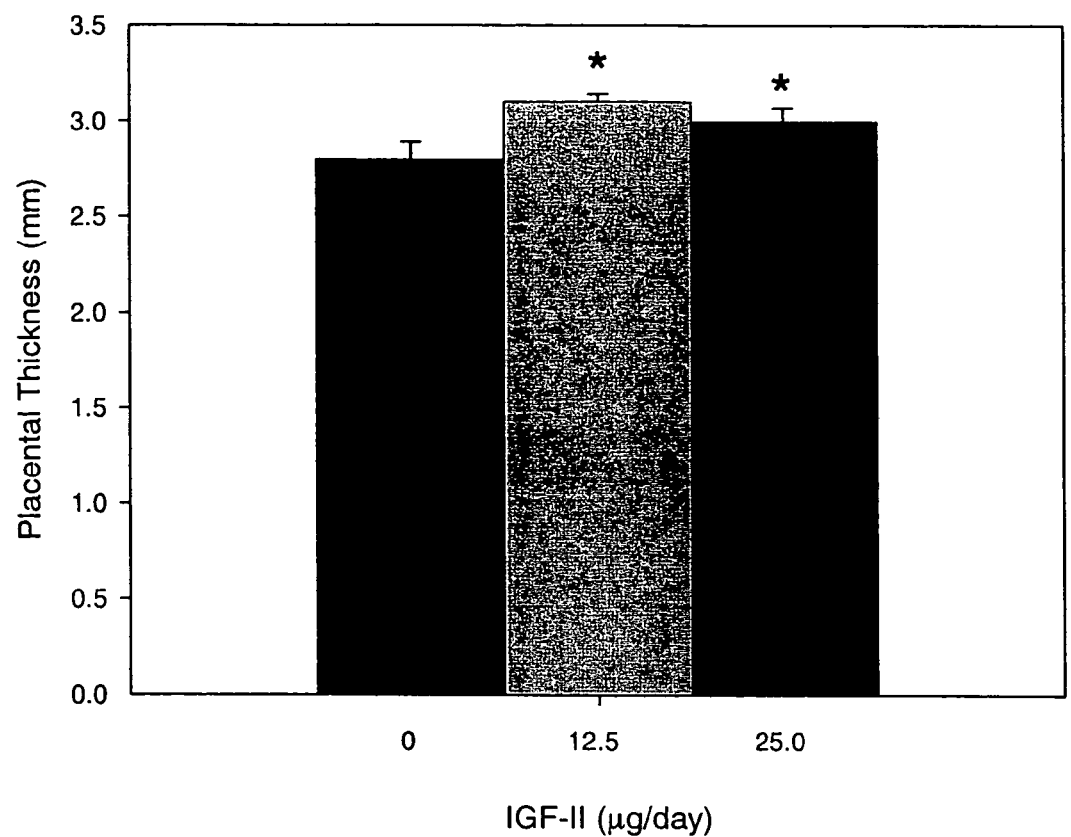
FIG. 10 illustrates the effect of treatment with IGF-II between days 2 and 18 of pregnancy in the mouse on placental thickness at day 18.
Figure 11:
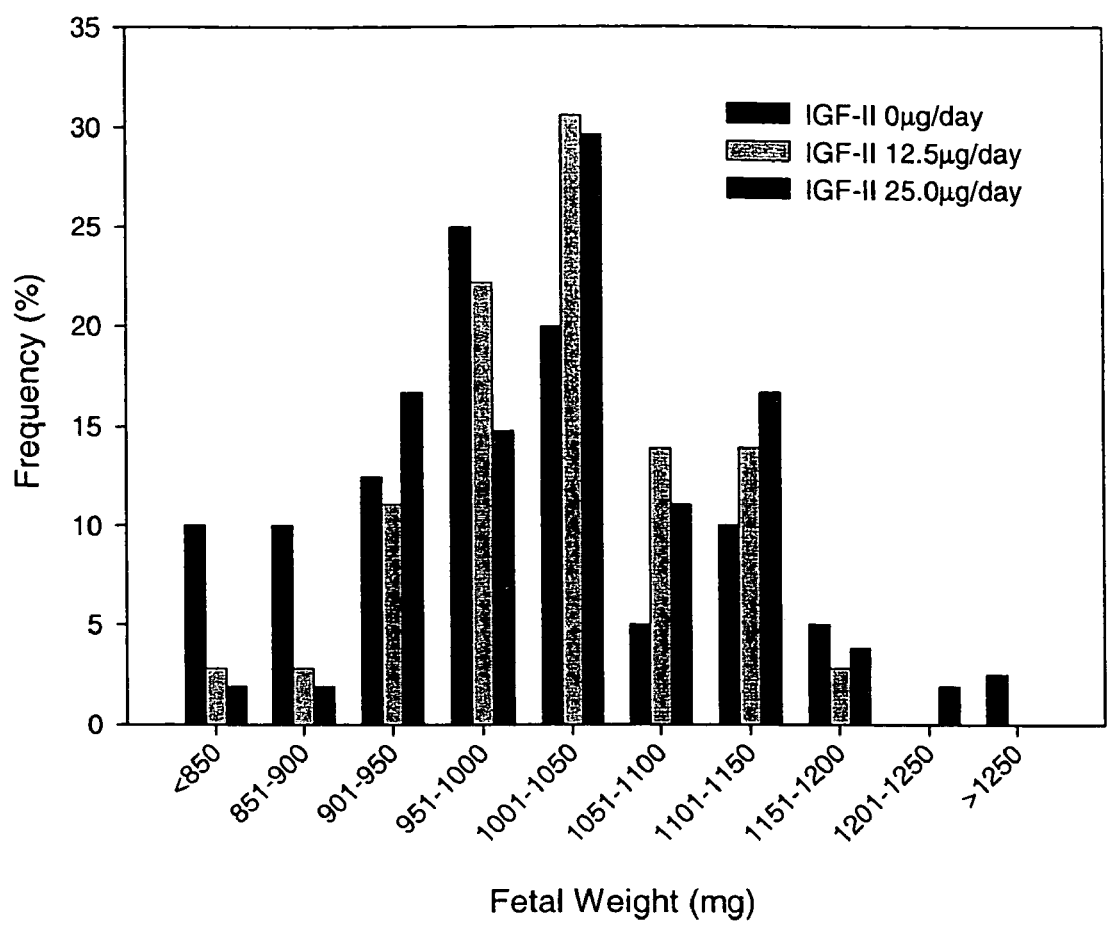
FIG. 11 illustrates the effect of treatment with IGF-II between days 2 and 18 of pregnancy in the mouse on the distribution of fetal weights at day 18.
Figure 12:
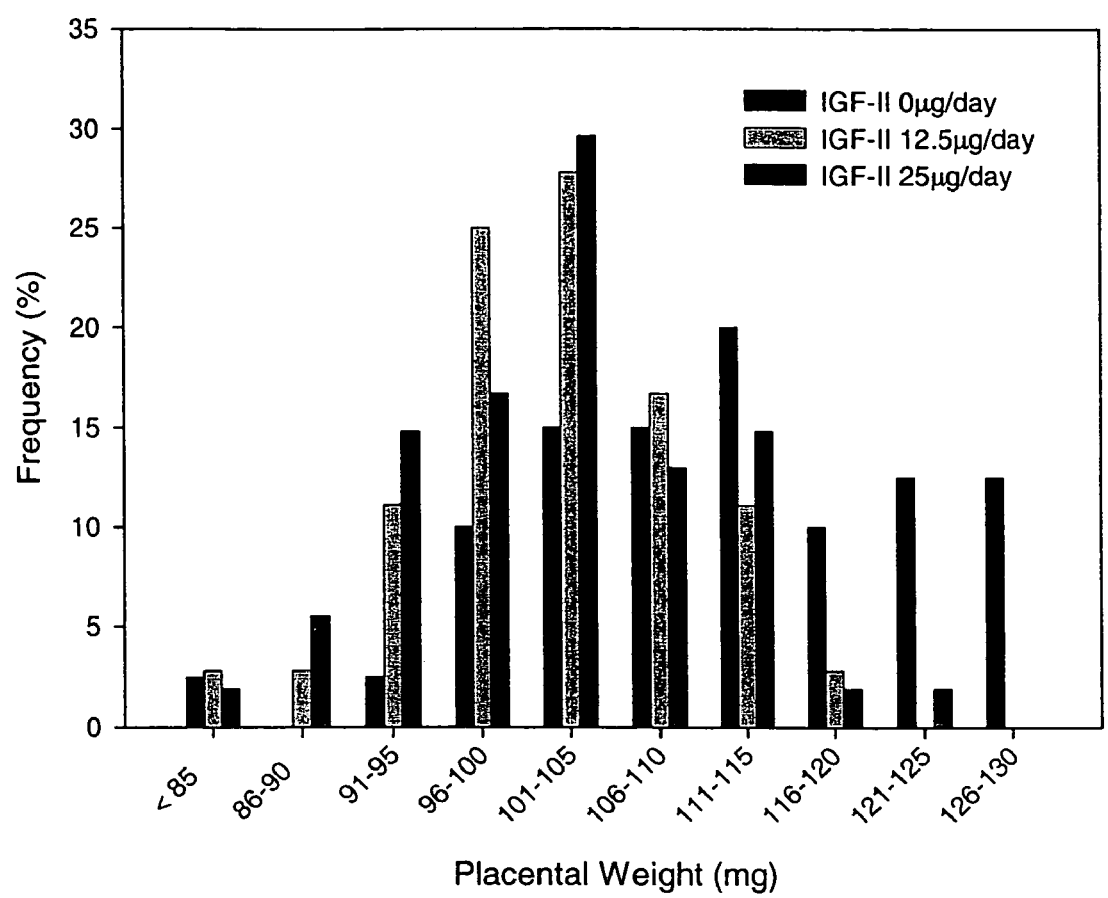
FIG. 12 illustrates the effect of treatment with IGF-II between days 2 and 18 of pregnancy in the mouse on the distribution of placental weights at day 18.

Treatment of pregnant mice with IGF-II between days 2 and 18 of pregnancy reduced placental weight in the high dose group by 4.8% (p=0.001) (FIG. 9), increased the thickness of the placenta by 5.6% (p=0.026) (FIG. 10). The distribution of fetal weights across litters was altered by treatment of the mother with IGF-II with a significant skew to the right in the 25 µg/day IGF-II group (p<0.0001) (FIG. 11). The distribution of placental weights across litters was also altered by treatment with IGF-II with a significant skew to the left in both treatment groups (p<0.0001) (FIG. 12)

Figure 13:
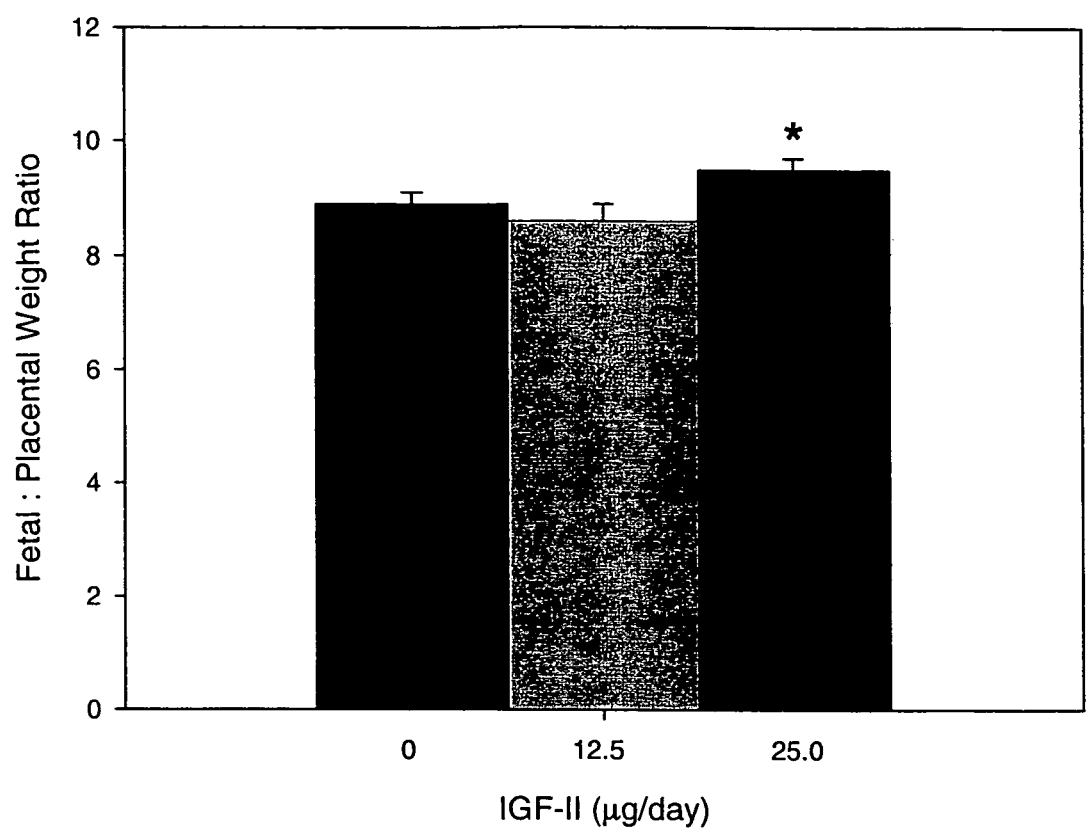
FIG. 13 illustrates the effect of treatment with IGF-II between days 2 and 18 of pregnancy in the mouse on the ratio of fetal to placental weights at day 18.

In addition treatment of pregnant mice with 25 µg/day IGF-II increased the ratio of fetal weight to placental weight by 6.9% (p=0.026) (FIG. 13). This is an indicator of placental functional capacity. A higher ratio suggests that more grams of fetus are produced for every gram of placenta. Thus the placenta is more efficient at extracting nutrients from the mother and transporting them to the fetus. Thus we have shown that treatment with IGF-II of the pregnant mouse improves placental and fetal development. However, treatment with IGF-II for the first half of pregnancy appears to be more efficacious than treatment throughout pregnancy with the same dose. It will be appreciated that the mice in the second replicate received the same amount of IGF-II each day from days 2-18 of pregnancy during which time maternal body weight was increasing. Hence the dose/day/kg was reducing, particularly in the second half of pregnancy when maternal weight gain is increasing. In addition, given that cytotrophoblasts are at their most invasive in the first half of pregnancy it may be most desirable to treat during this phase and may even have undesirable effects if continued throughout pregnancy.

It will be appreciated that the mice used in this experiment had normal placental IGF-II production. It is known that when the IGF-II gene is ablated in mice there is a considerable reduction in growth of the placenta and the fetus. It could be expected in embryos and/or their parents diagnosed with lower than normal capacity for IGF-II synthesis, the restoration of IGF-II to normal levels would have a still greater effect on placental development and hence fetal growth than is observed herein.

There was no difference in maternal weight gain or net carcass weight following treatment with IGF-II during pregnancy. Maternal weight gain was only related to litter size. Maternal net carcass weights were 24.1 0.4 g, 24.2 0.4 g and 24.9 0.4 g for control, 0.5 mg/kg/day IGF-II and 1.0 mg/kg/day IGF-II (p=0.262), respectively. This suggests that treatment with IGF-II throughout pregnancy at these doses does not increase cell proliferation in the mother.

The regulation of cytotrophoblast behaviour by IGF-II provides support for the notion that control of the cell exposure to IGF-II and latent TGFβ will affect stem cell (embryonic and adult) differentiation referred to hereinabove.

The invention has been described by way of example. The examples are not, however, to be taken as limiting the scope of the invention in any way. Modifications and variations of the invention such as would be apparent to a skilled addressee are deemed to be within the scope of the invention.

PUBLICATIONS CITED

Bennett S T & Todd J A (1996) Human type I diabetes and the insulin gene: principles of mapping polygenes. *Annu Rev Genetics* 30:343-370.

Bermingham J, Jenkins D, McCarthy T, O'Brien M (2000) Genetic analysis of insulin-like growth factor II and HLA-G in pre-eclampsia. *Biochem Soc Trans* 28:215-9.

Caniggia I, Mostachfi H, Winter J, Gassmann M, Lye S J, Kuliszewski & Post M (2000) Hypoxia-inducible factor-1 mediates the biological effects of oxygen on human trophoblast differentiation through TGFbeta(3). *J Clin Invest* 105, 577-587.

Djurovic S, Schjetlein R, Wisloff F, Haugen G, Husby H, Berg K (1997) Plasma concentrations of Lp(a) lipoprotein and TGF-beta1 are altered in preeclampsia. *Clin Genet* 52:371-376

Dommisse J & Tiltman A J (1992) Placental bed biopsies in placental abruption. *Br J Obstet Gynaecol* 99:651-4

Feldser D, Agani F, Iyer N V, Pak B, Ferreira G, Semenza G L (1999) Reciprocal positive regulation of hypoxia-inducible factor 1 and insulin-like growth factor 2. *Cancer Research* 59:3915-3918.

Floridon C, Nielsen O, Holund B, Sunde L, Westergaard J G, Thoms S G & Teisner B (1999) Localization and significance of urokinase plasminogen activator and its receptor in placental tissue from intrauterine, ectopic and molar pregnancies. *Placenta* 20: 711-721

Francis G L, McNeil K, Wallace J C, Ballard F J & Owens P C (1989) Sheep insulin-like growth factors I and II: sequences, activities and assays. *Endocrinology* 124: 1173-1183

Gargosky S E, Moyse K J, Walton P E, Owens J A, Wallace J C, Robinson J S, Owens P C 1990 Circulating levels of insulin-like growth factors increase and molecular forms of their serum binding porteins change with human pregnancy. *Biochemical and Biophysical Research Communications* 170:1157-1163

Genbacev O, Zhou Y, Ludlow J W & Fisher S J (1997) Regulation of human placental development by oxygen tension. *Science* 277, 1669-1672.

Godar S, Horesji V, Weidle U H, Binder B R, Hansmann C & Stockinger H (1999) M6P/IGFII-receptor complexes urokinase receptor and plasminogen for activation of transforming growth factor beta1. *Eur J Immunol* 29:1004-1013

Graham C H & Lala P K (1991) Mechanism of control of trophoblast invasion in situ. *J Cell Physiol* 148:228-234

Guidice L C, Mark S P & Irwin J C (1998) Paracrine actions of insulin-like growth factors and IGF binding protein-1 in non-pregnant human endometrium and at the decidual-trophoblast interface. *J Reprod Immunol* 39, 133-148.

Hamilton G S, Lysiak J J, Han V K M & Lala P K (1998) Autocrine-paracrine regulation of human trophoblast invasiveness by insulin-like growth factor (IGF)-II and IGF-binding protein (IGFBP)-1. *Exp Cell Res* 244:147-156

Huang L E, Arany Z, Livingston D M & Bunn H F (1996) Activation of hypoxia-inducible transcription factor depends primarily upon redox-sensitive stabilization of its alpha subunit. *J Biol Chem* 271, 32253-32259.

Irwin J C, Suen L F, Martina N A, Matk S P & Guidice L C (1999) Role of the IGF system in trophoblast invasion and pre-eclampsia. *Human Reprod* 14:90-96

Khong T Y, De Wolf F, Robertson W B & Brosens 1 (1986) Inadequate maternal vascular response to placentation in pregnancies complicated by pre-eclampsia and by small-for-gestational age infants. *Br J Obstet Gynaecol* 93:1049-1059

Khong T Y, Liddell H S, Robertson W B (1987) Defective haemochorial placentation as a cause of miscarriage: a preliminary study. *Br J Obstet Gynaecol* 94(7):649-55.

Lala P K & Graham C H (1990) Mechanisms of trophoblast invasiveness and their control: the role of proteases and protease inhibitors. *Cancer Metastasis Rev* 9(4):369-79

Morrish D W, Dakour J & Li H (1998) Functional regulation of human trophoblast differentiation. *J Reprod Immunol* 39:179-195

Odell S D & Day I N M (1998) Molecules in focus: insulin-like growth factor 11. *Int J Biochem Cell Biol* 30:767-771

Ong K K, Phillips Dl, Fall C, Poulton J, Bennett S T, Golding J, Todd J A, Dunger D B (1999) The insulin gene VNTR, type 2 diabetes and birth weight. *Nat Genet* 21:262-3.

Owens P C, Brinsmead M W, Waters M J & Thorburn G D (1980) Ontogenic changes in multiplication-stimulating activity binding to tissues and serum somatomedin-like receptor activity in the ovine fetus. *Biochem Biophys Res Commun* 96:1812-1820

Owens P C, Waters M J, Thorburn G D & Brinsmead M W (1985) Insulin-like growth factor receptor in fetal lamb liver: characterization and developmental changes. *Endocrinology* 117:982-92

Pijnenborg R, Bland J M, Robertson W B & Brosens I (1983) Uteroplacental arterial changes related to interstitial trophoblast migration in early human pregnancy. *Placenta* 4:397-414

Rebourcet R. de Ceuninck F, Deborde S, Willeput J & Ferre F (1998) Differential distribution of binding sites for $^{125}$I-insulin-like growth factor II on trophoblast membranes in human term placenta. *Biol Reprod* 58:37-44.

Schilling B & Yeh J (2000) Transforming growth factor beta(1), -beta(2), -beta(3) and their type I and II receptors in human term placenta. *Gynecol Obstet Invest* 50:19-23.

Tropepe V, Hitoshi S, Sirard C, Mak T W, Rossant J & van der Kooy D (2001) Direct neural fate specification from embryonic stem cells: a primitive mammalian neural stem cell stage acquired through a default mechanism. *Neuron* 30:65-78.

Wang G L, Jiang B H, Rueand E A & Semenza G L (1995) Hypoxia-inducible factor 1 is a basic-helix-loop-helix-PAS heterodimer regulated by cellular $O_2$ tension. *Proc Natl Acad Sci USA* 92, 5510-5514.

Zelzer E, Levy Y, Kahana C, Shilo B Z, Rubinstein M, Cohen B (1998) Insulin induces transcription of target genes through the hypoxia-inducible factor HIF-1alpha/ARNT. *Embo J* 17(17):5085-94.

The invention claimed is:

1. A method of improving a physiological characteristic in a pregnant female mammal, the physiological characteristic being selected from the group consisting placental growth, placental function, placental development and placental differentiation, the method comprising administering an effective amount of IGF-II to said pregnant female mammal in the first half of pregnancy, whereby said characteristic in said pregnant female mammal is improved.

2. The method of claim 1, wherein said effective amount of IGF-II comprises an amount sufficient to promote binding of said IGF-II to a cation independent mannose 6 phosphate receptor expressed on a cytotrophoblast cell.

3. The method of claim 1, wherein said IGF-II administered to said pregnant female mammal by subcutaneous delivery.

4. The method of claim 1, wherein said IGF-II is administered to said pregnant female mammal by vaginal pessary.

5. The method of claim 4, wherein said IGF-II is administered to said pregnant female mammal by subcutaneous delivery and vaginal pessary.

6. The method of claim 1, wherein said pregnant female mammal is selected from the group consisting of a human, a horse, a cow, a pig, a goat and a sheep.

* * * * *